(12) United States Patent
Stracener

(10) Patent No.: US 7,822,479 B2
(45) Date of Patent: Oct. 26, 2010

(54) CONNECTOR FOR IMPLANTABLE HEARING AID

(75) Inventor: Steve W. Stracener, Frederick, CO (US)

(73) Assignee: Otologics, LLC, Boulder, CO (US)

( * ) Notice: Subject to any disclaimer, the term of this patent is extended or adjusted under 35 U.S.C. 154(b) by 63 days.

(21) Appl. No.: 12/016,765

(22) Filed: Jan. 18, 2008

(65) Prior Publication Data

US 2009/0187233 A1    Jul. 23, 2009

(51) Int. Cl.
*A61N 1/00* (2006.01)
(52) U.S. Cl. .................................................. 607/57
(58) Field of Classification Search .................. 607/3, 607/37, 38, 57, 59; 439/172, 218, 502, 668
See application file for complete search history.

(56) References Cited

U.S. PATENT DOCUMENTS

| | | |
|---|---|---|
| 3,764,748 A | 10/1973 | Branch et al. |
| 3,838,468 A | 10/1974 | Armstrong |
| 4,462,401 A | 7/1984 | Burgio |
| 4,462,402 A | 7/1984 | Burgio et al. |
| 4,487,210 A | 12/1984 | Knudsen et al. |
| 4,498,461 A | 2/1985 | Hakansson |
| 4,516,820 A | 5/1985 | Kuzma |
| 4,606,329 A | 8/1986 | Hough |
| 4,612,915 A | 9/1986 | Hough et al. |
| 4,617,913 A | 10/1986 | Eddington |
| 4,628,907 A | 12/1986 | Epley |
| 4,655,776 A | 4/1987 | Lesinski |
| 4,756,312 A | 7/1988 | Epley |
| 4,774,933 A | 10/1988 | Hough et al. |
| 4,776,322 A | 10/1988 | Hough et al. |
| 4,800,884 A | 1/1989 | Heide et al. |
| 4,817,607 A | 4/1989 | Tatge |
| RE33,170 E | 2/1990 | Byers |
| 4,904,233 A | 2/1990 | H.ang.kansson et al. |
| 4,922,333 A | 5/1990 | Nutting et al. |
| 4,934,368 A | 6/1990 | Lynch |
| 4,957,478 A | 9/1990 | Maniglia |
| 4,957,507 A | 9/1990 | Lenkauskas |
| 4,982,434 A | 1/1991 | Lenhardt et al. |
| 4,998,333 A | 3/1991 | Skytta |
| 5,012,250 A | 4/1991 | Steeger |
| 5,015,224 A | 5/1991 | Maniglia |
| 5,024,224 A | 6/1991 | Engebretson |
| 5,038,781 A | 8/1991 | Lynch |
| 5,046,242 A | 9/1991 | Kuzma |
| 5,085,628 A | 2/1992 | Engebretson et al. |
| 5,105,811 A | 4/1992 | Kuzma |
| 5,144,952 A | 9/1992 | Frachet et al. |
| 5,217,011 A | 6/1993 | Bisch |

(Continued)

*Primary Examiner*—George Manuel
*Assistant Examiner*—Robert N Wieland
(74) *Attorney, Agent, or Firm*—Marsh Fischmann & Breyfogle LLP

(57) ABSTRACT

The present invention is directed to implantable hearing aid systems and provides for selective interconnection between two or more implantable components of a system. The inventive apparatus comprises a first connector interconnected to a distal end of a first signal cable that is connected to a first implantable component and a second connector interconnected to a distal end of a second signal second that is connected to a second implantable component. To facilitate routing of the signal cables, the male and female connectors are designed such that distal portions (e.g., mating ends) of the first and second signal cables may be juxtaposed (e.g., disposed side-by-side) when interconnected.

27 Claims, 6 Drawing Sheets

U.S. PATENT DOCUMENTS

| | | |
|---|---|---|
| 5,220,918 A | 6/1993 | Heide et al. |
| 5,277,694 A | 1/1994 | Leysieffer et al. |
| 5,282,858 A | 2/1994 | Bisch et al. |
| 5,324,311 A | 6/1994 | Acken |
| 5,345,509 A | 9/1994 | Hofer et al. |
| 5,358,514 A | 10/1994 | Schulman et al. |
| 5,370,689 A | 12/1994 | Causse |
| 5,404,407 A | 4/1995 | Weiss |
| 5,498,226 A | 3/1996 | Lenkauskas |
| 5,509,928 A | 4/1996 | Acken |
| 5,531,787 A | 7/1996 | Lesinski et al. |
| 5,545,219 A | 8/1996 | Kuzma |
| 5,624,376 A | 4/1997 | Ball et al. |
| 5,702,342 A | 12/1997 | Metzler et al. |
| 5,720,631 A | 2/1998 | Carson et al. |
| 5,730,628 A | 3/1998 | Hawkins |
| 5,772,575 A | 6/1998 | Lesinski et al. |
| 5,782,645 A | 7/1998 | Stobie et al. |
| 5,788,711 A | 8/1998 | Lehner et al. |
| 5,795,287 A | 8/1998 | Ball et al. |
| 5,797,834 A | 8/1998 | Goode |
| 5,800,336 A | 9/1998 | Ball et al. |
| 5,814,095 A | 9/1998 | Muller et al. |
| 5,857,958 A | 1/1999 | Ball et al. |
| 5,881,158 A | 3/1999 | Lesinski et al. |
| 5,913,815 A | 6/1999 | Ball et al. |
| 5,941,814 A | 8/1999 | Lehner et al. |
| 5,951,601 A | 9/1999 | Lesinski et al. |
| 5,984,859 A | 11/1999 | Lesinski |
| 5,993,376 A | 11/1999 | Kennedy |
| 6,001,129 A | 12/1999 | Bushek et al. |
| 6,005,955 A | 12/1999 | Kroll et al. |
| 6,038,484 A | 3/2000 | Kuzma |
| 6,039,685 A | 3/2000 | Bushek |
| 6,174,278 B1 | 1/2001 | Jaeger et al. |
| 6,272,382 B1 * | 8/2001 | Faltys et al. .................. 607/57 |
| 6,517,476 B1 | 2/2003 | Bedoya et al. |
| 6,743,055 B1 * | 6/2004 | Flynn et al. ................ 439/651 |
| 2006/0183965 A1 | 8/2006 | Kasic et al. |
| 2007/0099487 A1 * | 5/2007 | Osypka ..................... 439/502 |
| 2008/0103551 A1 * | 5/2008 | Masoud et al. ................ 607/59 |

* cited by examiner

CONNECTOR FOR IMPLANTABLE HEARING AID

FIELD OF THE INVENTION

The present invention relates to semi and fully-implantable hearing instruments, and more particularly, to an interconnection apparatus and method that simplifies implant procedures and facilitates selective removal/replacement of one or more of the implanted components of a hearing instrument.

BACKGROUND OF THE INVENTION

Implantable hearing devices stimulate internal components of the auditory system and are generally classified into one of two types, namely fully implantable hearing instruments and semi-implantable hearing instruments. In a fully implantable hearing device, the entire instrument is implanted. In a semi-implantable hearing instrument, some of the components, typically the microphone, power supply, and speech signal processor, are externally worn, while the auditory stimulator and key support functions are implanted within the auditory system. The externally worn portion communicates transcutaneously with the implanted portion to provide audio signals that the implanted portion uses to stimulate to the auditory system.

Implanted hearing devices are typically used by individuals with significant loss of hearing function or damage to the auditory system. As a result, they differ in the manner by which the signal is processed and delivered to the patient. The processing step, known in the art as Speech Signal Processing ("SSP"), may include a number of steps such as amplification, frequency shaping, compression, etc. The steps in the SSP are determined by the design of the hearing device, while the particular internal values used in the steps are generated from prescriptive parameters determined by an audiologist. Once a speech processor receives an audio signal (e.g., from a microphone) that is indicative of ambient acoustic signals, a drive signal is produced and provided to an implanted stimulation device that stimulates the hearing impaired person's auditory system. The auditory stimulation may be done acoustically, mechanically, or electrically as a function of the type and severity of the hearing loss in the hearing impaired individual.

By way of example, one type of implantable mechanical stimulator includes an electromechanical transducer having a magnetic coil that drives a vibratory actuator. The actuator is positioned to interface with and stimulate the ossicular chain of the patient via physical engagement. (See e.g., U.S. Pat. No. 5,702,342). In this regard, one or more bones of the ossicular chain are made to mechanically vibrate, which causes the ossicular chain to stimulate the cochlea through its natural input, the so-called oval window. In contrast, a cochlear implant system utilizes an electrode that is inserted into the cochlea to provide electrical stimulation.

In addition to implantable auditory stimulators, other components of implantable hearing instruments may be located subcutaneously (i.e, implanted). By way of example, such additional components may include a receiver for receiving RF signals from an external transmitter and processing electronics to process the received signals and provide an appropriate output signal to an implantable auditory stimulator. In this regard, most implantable hearing devices (i.e., fully and semi-implantable) include an auditory stimulator and an implanted housing that houses such additional components.

In conjunction with implant procedures for attaching an implantable auditory stimulator to the an auditory component of a patient, the various implanted components of a given system may entail positioning at a number of differing locations proximal to the skull (e.g., mastoid process) of a given patient. As will be appreciated, such positioning may require a number of different surgical steps, including for example, the placement of an implantable auditory stimulator through a hole drilled into the mastoid process. Given such positioning requirements, initial component placement can be a challenging procedure and removal/repositioning of selected implanted components of a given implantable hearing aid system (e.g., for reprogramming, replacement, servicing, etc.) may be problematic after the initial implant procedure.

SUMMARY OF THE INVENTION

In view of the foregoing, one objective is to provide an implantable connector apparatus and method that facilitates the initial positioning of multiple implanted components comprising a given implantable instrument.

An additional objective is to provide an implantable instrument and associated method that facilitates selective replacement, servicing and/or repositioning of implantable components of the implantable instrument.

The above-noted objectives and additional advantages may be realized in various aspects of the current invention, which is directed to subcutaneous connectors that facilitate cable management and implant component placement. Such connectors allow for the interconnection of separate implantable components of an implantable instrument including, without limitation, implantable hearing instruments to allow for signal transmission between the implanted components. More specifically, aspects of the present invention are directed towards an in-line connection in between individual components of an implantable instrument. In this regard, such individual components may each include a signal cable having a connector on a distal end thereof that allows for connection with a mating connector on another signal cable. Various aspects of the present invention allow for interconnecting a male connector disposed on the end of a first signal cable to a female connector on disposed on a second signal cable. In this regard, internal conductors of the first signal cable interconnected to the male connector may be electrically connected to internal conductors of a female conductor and, hence, the internal conductors of the second signal cable. Further, once connected, in addition to allowing for signal transmission between the separate implantable components, the male and female connectors may be sealably interconnected to prevent intrusion of, for example, fluids. In order to facilitate routing of the signal cables, the male and female connectors are designed such that distal portions (e.g., mating ends) of the first and second signal cables may be juxtaposed (e.g., disposed side-by-side) when interconnected. For instance, such signal cables may be substantially parallel when interconnected. Though discussed primarily in conjunction with implantable hearing instruments, it will be appreciated that aspects of the subcutaneous connectors may be utilized with other implantable instruments having multiple implantable components that are interconnected by one or more cables.

According to a first aspect of the present invention, an implantable hearing instrument is provided having an implantable male connector that is fixedly connected to a distal end of a first signal cable and an implantable female electrical connector that is fixedly connected to a distal end of a second signal cable. These first and second signal cables may be operatively interconnected to first and second components of an implantable hearing instrument. The female connector further includes a housing to which the second cable may be sealably received. In this regard, conductors within the second cable may extend into the housing and be connected to one or more internal contact members. The female connector includes a receiving port that is disposed proximate to a location where the second cable connects to the housing. When the male connector is disposed within the receiving port, the distal ends of the first and second cables may be juxtaposed. Further, when the male and female connectors are selectively interconnected, they provide subcutaneous signal transmission between the first and second implantable instrument components. That is, the male connector may contact the contact members of the female connector and thereby create an electrical path between the first and second components of the implantable instrument.

In one arrangement, the first and second cables extend away from the housing of the female connector in a substantially common direction. That is, the first and second cables may be side-to-side as they exit the housing when the male connector is disposed within the female connector. In this regard, the female connector may effectively define a U-shaped connector wherein the first cable is, for example, fixedly interconnected to a first leg of the U-shape and the second cable is releasably connected to the second leg of the U-shape. Stated otherwise, the receiving port may form a substantially cylindrical recess having an open and closed end. Such a cylindrical recess may define a first reference axis, and a central axis of the cable that is fixedly connected to the female connector may define a second reference axis. In one arrangement, these reference axes may be parallel as they extend away from the female housing in a common direction. In a second arrangement, these first and second references axes may be disposed at an angle such that they intersect (e.g., when viewed in a plan view). In such an arrangement, an included angle between these reference axes may be less than about 45 degrees. In a further arrangement, the angle between the first and second reference axes may be less than 20 degrees, and in a further arrangement, the included angle may be less than about 15 degrees.

In one arrangement, the female connector includes at least two internal contact members. In this regard, each of the cables also includes at least first and second conductors/wires. Accordingly, at least two conductors may be interconnected between the first and second implantable components. In one arrangement, the first and second contact members within the female connector include openings therethrough. Accordingly, the male connector may be sized for receipt through these openings. For instance, the male connector may include a cylindrical body having a tip conductor and a sleeve conductor that is separated by an insulating ring. In this regard, the male connector may be similar to a IS-1 connector. In such an arrangement, the tip conductor/sleeve conductor of the male connector and the openings through the first and second contact members may be coaxially disposed when the male connector is disposed within the female connector. However, it will be appreciated that additional conductors (e.g., three or more) may be interconnected. That is, each of the female and male connectors may have three or more contact conductors.

To maintain the male and female connectors in an interconnected orientation, the apparatus may further include at least one locking member that is positionable through the housing of the female connector to selectively lock the male connector in an interconnected relationship. In one arrangement, the locking member(s) may be threaded members.

The internal conductor(s) of the female and male connectors, as well as any locking members, if included, may comprise substantially the same conductive materials so as to substantially reduce or avoid any galvanic potential. By way of example, such a conductive metal may comprise of metal selected from the group consisting of titanium, titanium alloys, gold and platinum. Further, in this regard, one or more of the components forming the implantable components may be disposed within a housing comprising a metal selected from the above-noted group.

Generally, male and female conductors are fixedly connected to the distal ends of the cables associated with the implantable instrument components. It will be appreciated that the opposing end of each cable may be fixedly or releasably interconnected to their respective implantable instrument component.

Although any implantable components may be interconnected, in one arrangement, one of the implantable components is an auditory stimulator of an implantable hearing instrument. Such an auditory stimulator may include, without limitation, a middle ear transducer, a cochlear electrode and/or a vegal nerve stimulator. In such an arrangement, the other component will generally be a component that provides a stimulation signal for the auditory component. In this regard, another component may include, without limitation, a fully implantable hearing instrument including an implantable microphone and signal processor or a partially implantable hearing instrument including receiving means for transcutaneously receiving auditory stimulation signals. Stated otherwise, the second component will generally generate or otherwise provide a signal and/or power for receipt by the auditory stimulator.

In conjunction with the present invention, an inventive method for use of an implantable instrument is also provided. In particular, the method may include positioning a first component of an implantable instrument at a first subcutaneous location relative to a patient's skull wherein the first component includes a first cable having a female connector connected to a distal end thereof. The method may further include locating a second component of the implantable instrument at a second subcutaneous location relative to the patient's skull wherein the second component includes a second cable having a male connector at its distal end. Upon positioning/locating the components, the male connector may be inserted within the receiving port of the female connector to establish a sealed electrical interconnection between the corresponding internal conductors thereof. This may allow for subcutaneous signal transmission between the first and second components. Further, the distal portions of the first and second cables may be juxtaposed when the male connector is inserted within the female connector.

Juxtapositioning of the first and second cables may facilitate the implant procedure. In this regard, it will be appreciated that once the first and second instrument components are located subcutaneously, the cables attached thereto may be routed out of, for example, a common incision utilized to insert the first and second components. Accordingly, interconnection of the first and second cables (e.g., the male connector into the female connector) may be performed externally to the patient. This may facilitate, for example, advancing a threaded locking member to fixedly connect the male connector within the female connector. Furthermore, once such interconnection is made and the cable ends are disposed side by side in a single connector, the connector may be used to subcutaneously position the mating ends of the signal cables. This may simplify subcutaneous positioning of the interconnected cables. Further, the overall length of the connector may be reduced in comparison with a series type (e.g., end to end) connector.

Numerous additional features and advantages of the present invention will become apparent to those skilled in the art upon consideration of the further description that follows.

DETAILED DESCRIPTION

Reference will now be made to the accompanying drawings, which at least assist in illustrating the various pertinent features of the present invention. In this regard, the following description of a subcutaneous connector utilized with an implanted hearing aid device is presented for purposes of illustration and description. Furthermore, the description is not intended to limit the invention to the form disclosed herein. Consequently, variations and modifications commensurate with the following teachings, and skill and knowledge of the relevant art, are within the scope of the present invention. The embodiments described herein are further intended to explain the best modes known of practicing the invention and to enable others skilled in the art to utilize the invention in such, or other embodiments and with various modifications required by the particular application(s) or use(s) of the present invention.

Figure 1:
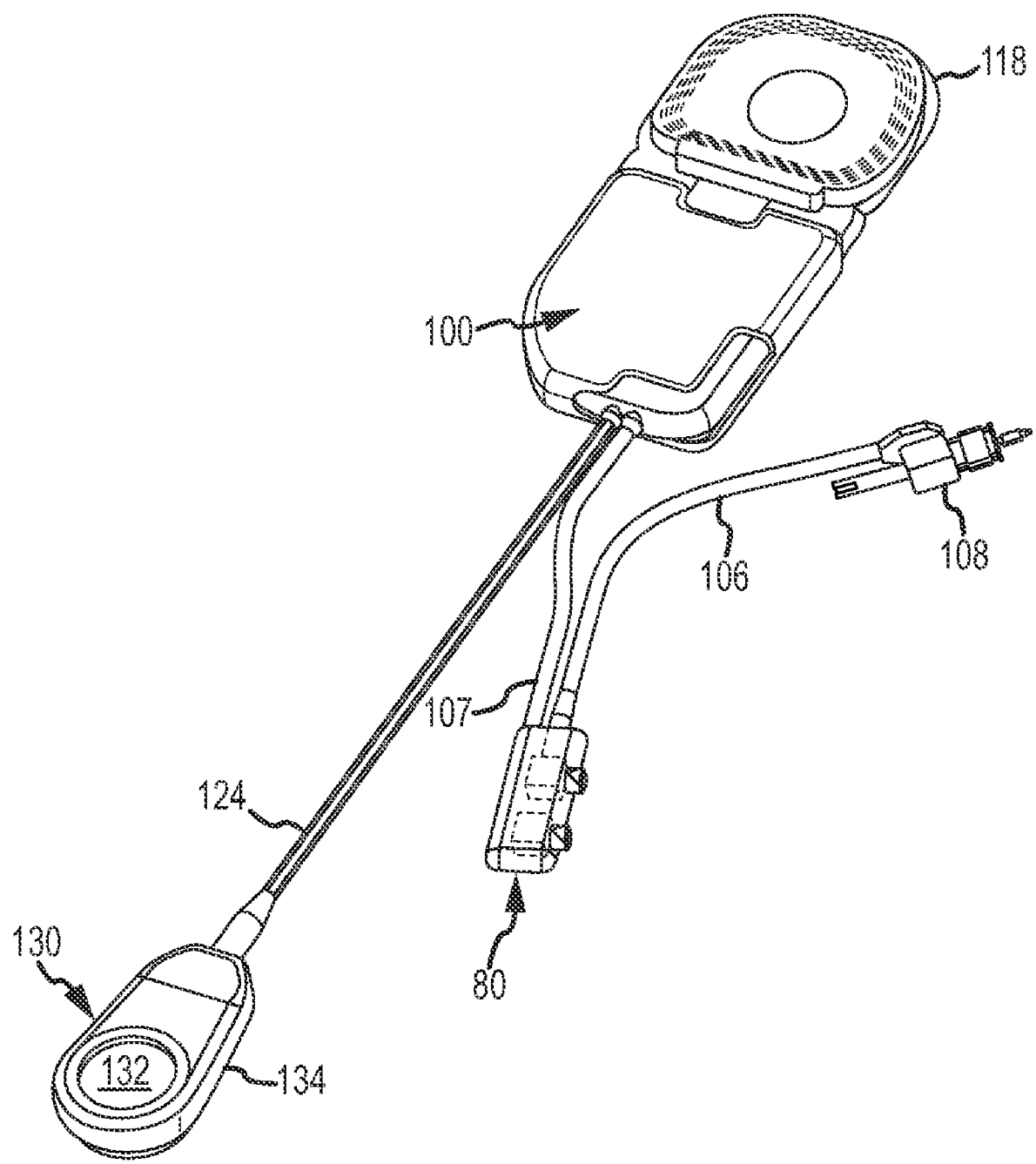
FIG. 1 is a perspective view of one embodiment of the present invention as implemented with an implantable hearing instrument.
Figure 2:
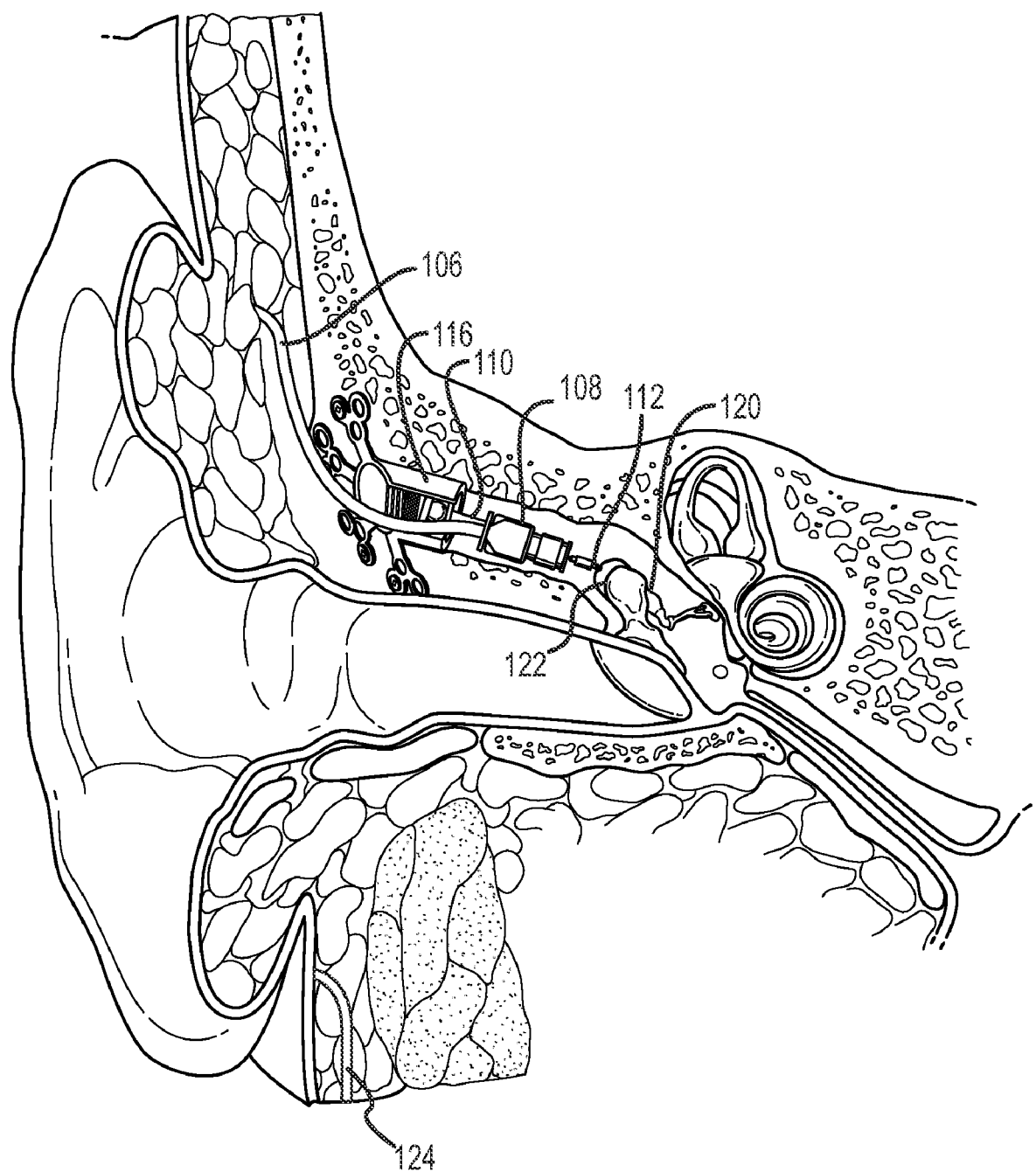
FIG. 2 illustrates the positioning and interconnection of various components in a fully implantable embodiment of the present invention.
Figure 3:
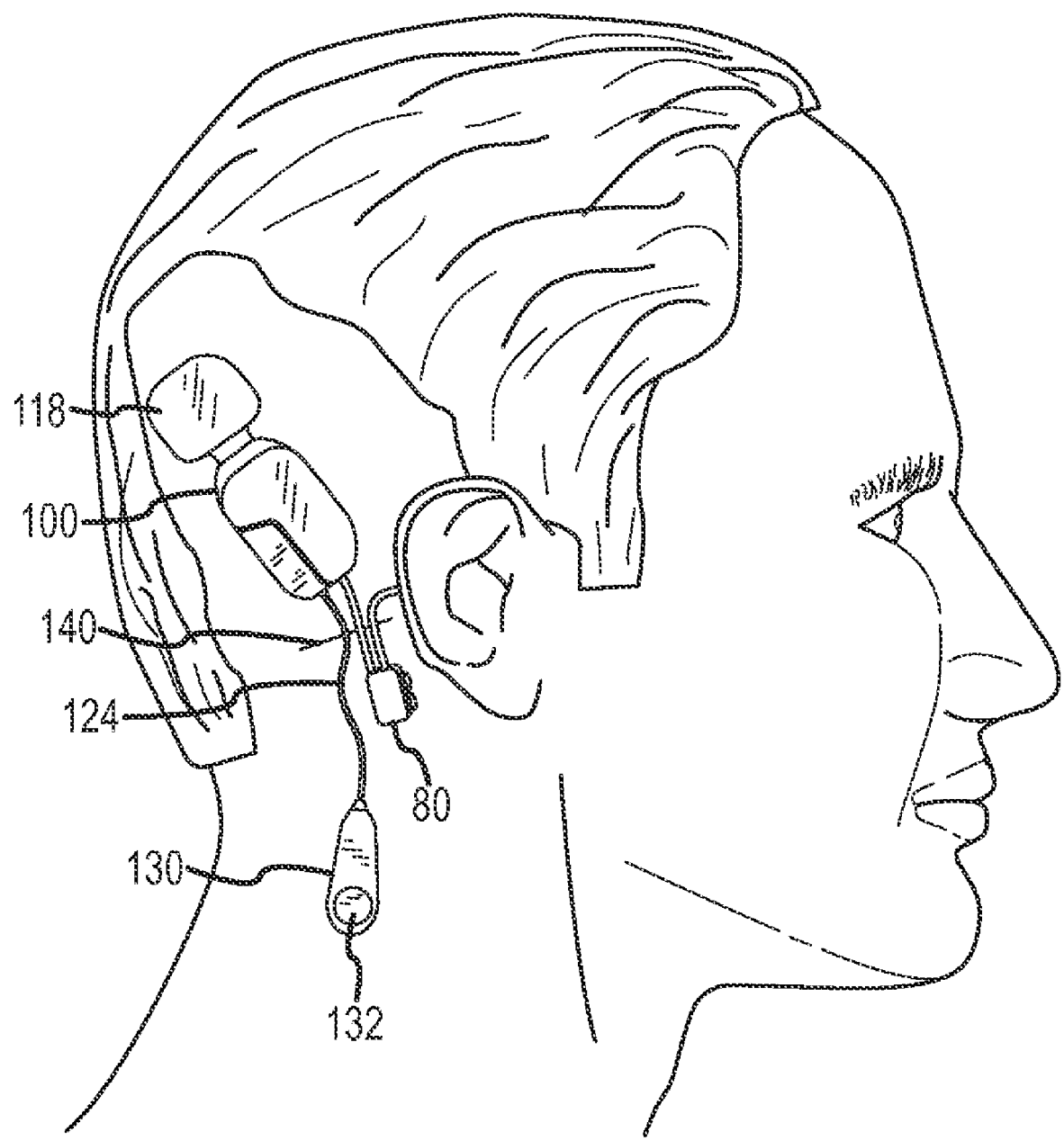
FIG. 3 is a side view of the system of FIG. 1 placed on a patient's skull.

FIGS. 1-3 illustrate one embodiment and application of the present invention. As illustrated, the embodiment is utilized in a fully implantable hearing instrument system that provides mechanical stimulation to the middle ear of a patient. As will be appreciated, certain aspects of the present invention may be employed in conjunction with different implantable systems including but not limited to semi-implantable hearing instruments as well as inner ear hearing instruments (e.g., cochlear implants), and therefore, the illustrated application is for purposes of illustration and not limitation.

In the illustrated system, a biocompatible implant housing 100 is located subcutaneously on a patient's skull. The implant housing 100 includes a signal receiver 118 (e.g., comprising a coil element) and is interconnected to a microphone assembly 130 via a signal cable 124. The implant housing 100 may be utilized to house a number of components of the implantable hearing instrument. For instance, the implant housing 100 may house an energy storage device and a signal processor. Various additional processing logic and/or circuitry components may also be included in the implant housing 100 as a matter of design choice. In the present arrangement, the signal processor within the implant housing 100 is electrically interconnected to a transducer 108. As will be further discussed herein, the transducer 108 is connected to the implant housing via first and second signal cables 106, 107. These signal cables 106, 107 are connected by a connector 80 that allows for selective connection and disconnection.

As illustrated in FIG. 2, the transducer 108 is supportably connected to a positioning system 110, which in turn, is connected to a bone anchor 116 mounted within the patient's mastoid process (e.g., via a hole drilled through the skull). The transducer 108 includes a connection apparatus 112 for connecting the transducer 108 to the ossicles 120 of the patient. In a connected state, the connection apparatus 112 provides a communication path for acoustic stimulation of the ossicles 120, e.g., through transmission of vibrations to the incus 122.

Referring to FIGS. 1, and 3, it is noted that microphone assembly 130 in the present embodiment is a pendant microphone that is connected to the implant housing via a signal cable 124. Use of such a pendant microphone allows the microphone assembly 130 to be spaced from the implant housing 100 such that it is need not mounted to the skull of a patient. Such spacing may facilitate vibration attenuation as well as reduce the number of components that need to be mounted in/on the limited space on the skull near the patient's ear (e.g., mounted near the mastoid process). However, it will be appreciated that in other embodiments, the microphone may be mounted or integrally formed on or within the implant housing 100.

The microphone assembly 130 includes a diaphragm 132 that is positioned to receive ambient acoustic signals through overlying tissue, a microphone transducer (not shown) for generating an output signal indicative of the received ambient acoustic signals, and a housing 134 for supporting the diaphragm 132 relative to the transducer. As shown, the microphone assembly 130 may be mounted to soft tissue of the neck of the patient and the cable 124 interconnecting the implant housing 100 and the microphone assembly 130 may be routed subcutaneously to the implant housing 100.

During normal operation, acoustic signals are received subcutaneously at the diaphragm 132 of the microphone assembly 130. The microphone assembly 130 generates an output signal that is indicative of the received acoustic signals. The output signal is provided to the implant housing 100 via the signal cable 124. Upon receipt of the output signal, a signal processor within the implant housing 100 processes the signals to provide a processed audio drive signal, via the connected signal cable 106 and 107, to the transducer 108. As will be appreciated, the signal processor may utilize digital processing techniques to provide frequency shaping, amplification, compression, and other signal conditioning, including conditioning based on patient-specific fitting parameters. The audio drive signal causes the transducer 108 to transmit vibrations at acoustic frequencies to the connection apparatus 112 to effect the desired sound sensation via mechanical stimulation of the incus 122 of the patient. Similar processes may be utilized for cochlear stimulation devices.

As noted, during implantation of an implantable hearing instrument, a hole is typically formed in or near the mastoid process of a patient to allow an auditory stimulator (e.g., mechanical transducer, floating mass transducer, cochlear stimulator, etc) to access an auditory component of the middle and/or inner ear. Irrespective of the type of auditory stimulator utilized, a signal cable is typically routed from the auditory stimulator to an implant housing that is typically mounted to the surface of the skull of a patient. Accordingly, this signal cable must be electrically interconnected to the implant housing in order to receive stimulation signals. To facilitate the implant procedure, as well as to permit upgrading of the electronics, batteries etc, located in the implant housing, it is desirable that the signal cable between the auditory stimulator and the implant housing permit selective connection and disconnection.

It has further been determined that in many instances it may be desirable to make such a connection at a location removed from the implant housing. That is, it may be desirable to make an in-line connection where the signal cable 106 extending from the auditory and the signal cable 107 extending from the implant housing are connected at a location between the implant housing 100 and the auditory stimulator 108. For instance, it is often necessary or desirable to secure the implant housing to the skull prior to electrically connecting the housing to the auditory stimulator. Generally, bone is removed to form a "bed" for the housing. If the signal cable from the auditory stimulator plugs into the housing, additional bone may need to be removed to provide access to a connection port, which may lengthen a surgical procedure. Further, if such a connection on the implant housing includes locking elements (e.g., set screws), the size or number of the surgical incision(s) may have to be increased to access such locking elements. Still further, due to the minimum bending radius of the signal cable(s), it may be difficult to route the signal cable between the auditory stimulator and the implant housing. Stated otherwise, direct connection to the implant housing may limit where the housing is located on the skull of a patient. Another potential drawback to utilizing an in-line connection between the first and second signal cables is the resulting length of the connection. That is, if an in-line connection is utilized where male and female connectors on the distal ends of the cables 106, 107 are interconnected in series, the resulting connected cable between the housing 100 and the auditory stimulator 108 may include a relatively long rigid section that may be difficult to subcutaneously position.

Figure 4B:
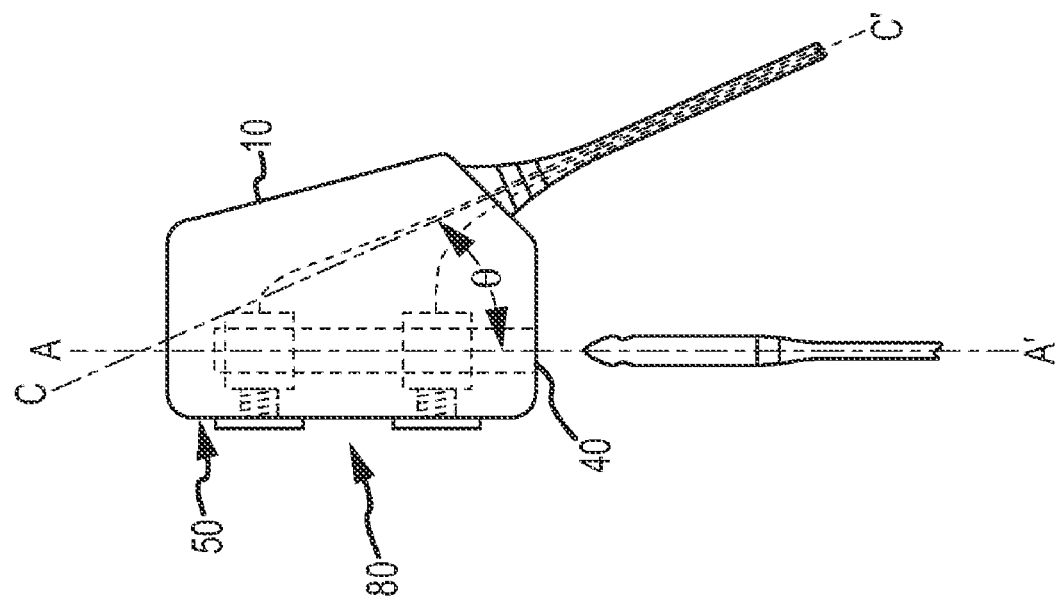
FIG. 4B is a plan view of a second embodiment of the present invention.
Figure 4A:
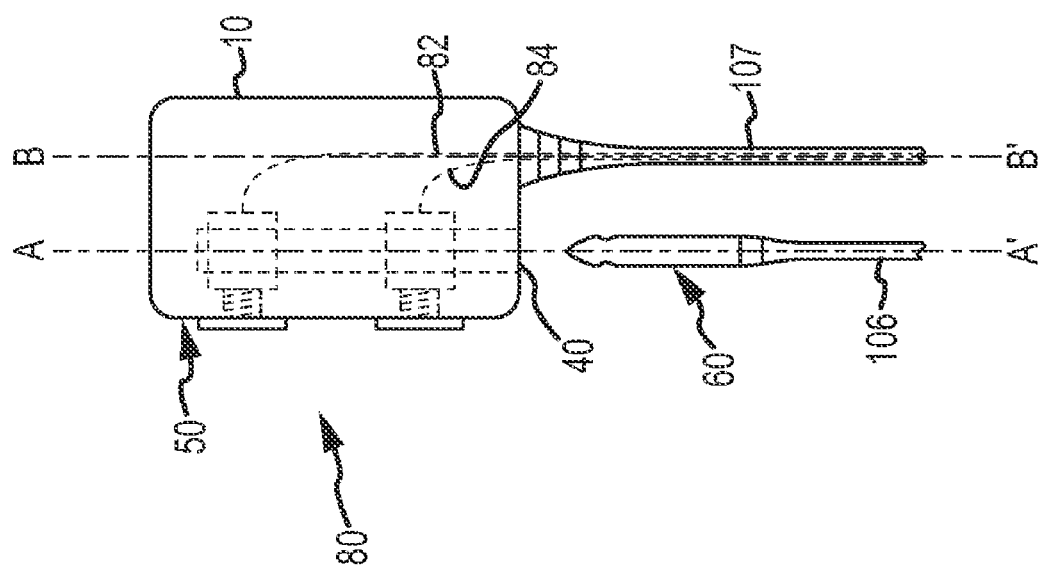
FIG. 4A is a plan view of a first embodiment of the present invention.

Accordingly, the connector 80 of the present invention utilizes a configuration that alleviates many of these routing issues and provides additional benefits. As illustrated in FIGS. 4A and 4B, various embodiments of the connector 80 utilize a female connector 50 that is interconnected to a distal end of one of the signal cables 107. The female connector 50 is adapted to receive a male connector 60 (i.e., disposed on the end of the other cable 106) from substantially the same end/direction as the cable 107 enters the housing 10 of the female connector 50. As illustrated in FIGS. 4A and 4B, this results in the first and second cables 106, 107 being juxtaposed (e.g., substantially side-to-side) when the male connector 60 is inserted within the female connector 50. That is, the connectors 80 illustrated in FIGS. 4A and 4B are return connectors where a first signal line enters a first end of the connector 80 and the second signal line returns out of the connector 80 in substantially the same direction.

In the embodiment of FIG. 4A, a central axis A-A' of a receiving port/recess 40 of the female connector 50 defines a first reference axis. Likewise, the center axis of the cable 107 that is fixedly connected to the female connector 50 defines a second reference axis B-B' (e.g., when that cable 107 is tensioned directly away from the connector). That is, the cable 107 enters the housing 10 of the female connector 50 along a predetermined axis as defined by its interconnection to the housing 10 and the central axis of the cable 107. In the embodiment of FIG. 4A, these reference axes are substantially parallel and the connector defines a 180° return connector. In contrast, in the embodiment of FIG. 4B, the reference axis C-C' defined by the cable 107 may be offset relative to the reference axis A-A' defined by the central axis of the recess 40. For instance, in a plan view, these axes may intersect. However, an included angle $\Theta$ between these axes may be and acute angle. That is, $\Theta$ may be less than 90 degrees, and more preferably less than about 45 degrees, and yet more preferably less than about 20 degrees or even 15 degrees. What is important is that the cables enter and exit from a substantially common end of the housing of the connector 80.

Use of a such return connector may facilitate positioning of the components relative to the patient's skull. For instance, as illustrated in FIG. 3, the ends of the signal cables 106, 107 may be routed outside an incision 140. Once the implant housing 100 and an auditory stimulator (e.g., 108, not shown) are subcutaneously positioned, the cables 106, 107 may be routed out of the incision 140. At such time, the signal lines 106, 107 may be connected (e.g., external to the patient) and then reinserted through the incision 140 to a subcutaneous location. As both cables are side-by-side, the connector 50 may facilitate insertion of the signal lines back into the incision 140 to a subcutaneous location therein.

Figure 5:
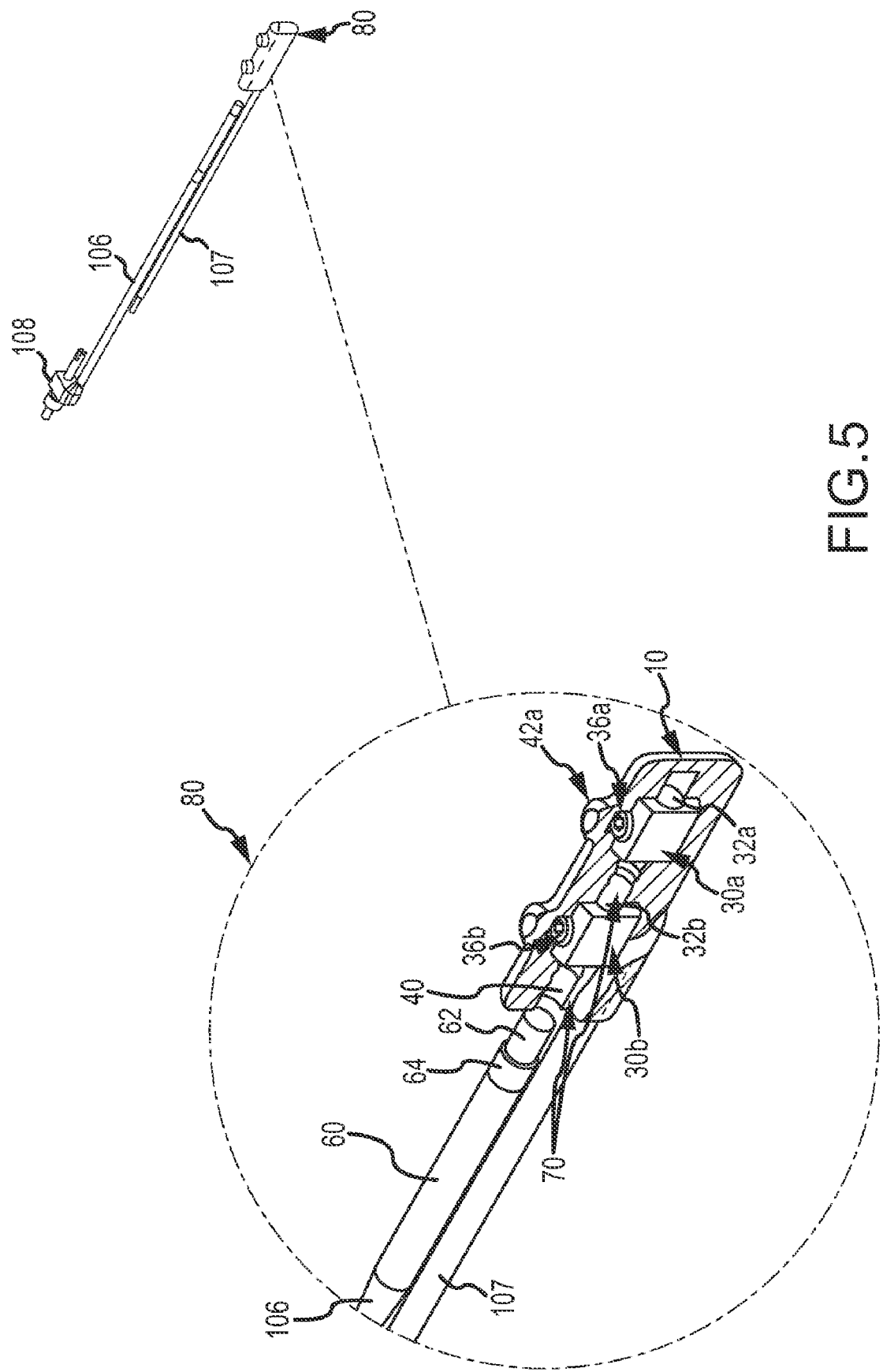
FIG. 5 is a partial cross-sectional, isometric view of the embodiment of FIG. 4A.

FIGS. 1, 4A, and 5 illustrate one embodiment of a 180° return connector 80 as implemented in an implantable hearing system. As noted, the return connector 80 includes an implantable female connector 50 having a connector housing 10 that is connected to the implant housing 100 via signal cable 107. The housing 10 sealably supports various components to define a receiving port. In the present embodiment, the signal cable 107 is permanently and sealably attached to the connector housing 10. This allows individual signal wires or conductors disposed within the signal cable 107 to pass into the housing 10. Generally, the connector housing 10 has a width that is slightly greater than the width of the juxtaposed signal cables. The length and thickness are also kept to a minimum. In this regard, the housing 10 is sized such that it does not require a bone bed be formed for the connector 80.

The connector housing 10 houses a female electrical connection port or 'jack' for receiving a mating male electrical connector or 'plug' that is connected to the end of the signal cable 106 connected to the auditory stimulator. As shown, the connector housing 10 includes first and second electrical contact blocks 30a and 30b which are electrically interconnected to individual signal wires 82, 84 that lead to the implant housing 100 via the fixedly attached signal cable 107. See FIG. 4A. These signal wires 82, 84 may be interconnected to their respective contact blocks 30A, 30B in any appropriate manner (e.g., soldered, welded, etc.) and may extend to and connect with separate outputs of a processor within the implant housing 100. When the male connector 60 of the second signal cable 106 is inserted within the female port of the female connector 50, the signal wires may carry stimulation signals as well as operating power for receipt by the auditory stimulator 108.

In order to receive and make electrical contact with the male connector 60, aligned openings 32a and 32b are provided through electrical contact blocks 30a and 30b. See FIGS. 5, 6A and 6B. Relatedly, an elongated recess 40 is defined in the connector housing 10, wherein the recess 40 is coaxially aligned with the openings 32a and 32b of the electrical contact blocks 30a and 30b so as to collectively define the female connection port for receiving the elongated male connector 60. The male connector 60 provides for electrical connection between electrical contact blocks 30a and 30b and the auditory stimulator 108 disposed at a distal end of the signal cable 106.

Once connected, the implant housing 100 may deliver power and acoustic data signals to the auditory stimulator 108. That is, a processor unit in the implant housing 100 may generate an output signal that is communicated to the auditory stimulator 108 via two or more conductors 82, 84 disposed within the cable 107, wherein mating conductors in each cable are electrically interconnected upon insertion of the male connector 60 into the female connector within connector housing 10. As may be appreciated, in the present embodiment such a processor unit output signal is employable by the auditory stimulator 108 to stimulate the ossicular chain and/or oval window of a patient so as to provide for enhanced patient hearing.

Figure 6A:
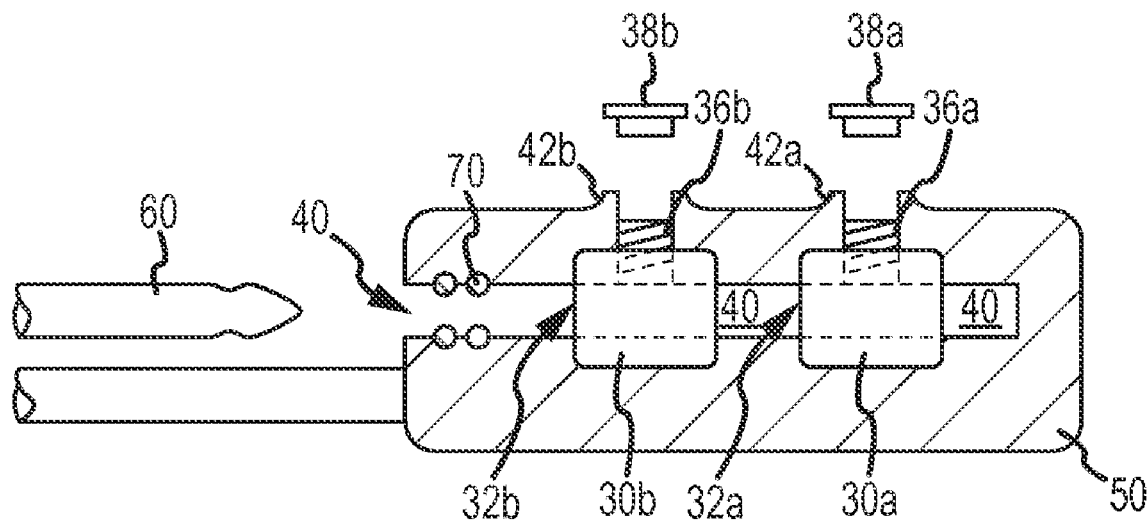
FIG. 6A is a plan, partial cut-away view showing the female connector of FIGS. 4A and 5.
Figure 6B:
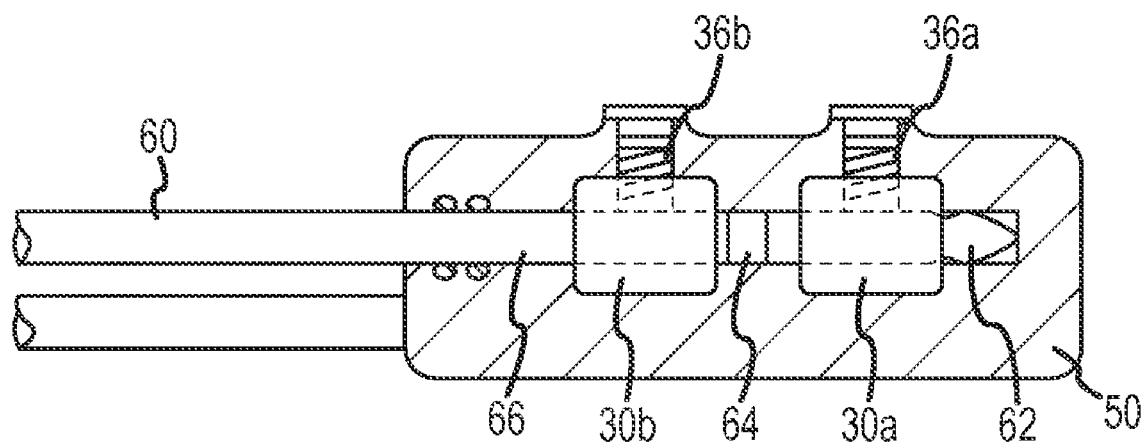
FIG. 6B is a plan, partially cut away showing insertion of the male connector in the female connector of FIG. 6A.

As shown in the FIGS. 6A and 6B, the illustrated embodiment may further comprise first and second locking members 36a and 36b which are selectively positionable through openings 42a and 42b defined through a surface of the connector housing 10 (e.g., a side surface or top surface thereof). More particularly, locking members 36a and 36b may be externally threaded (e.g., set screws) for threadable engagement with internally threaded surfaces provided in corresponding side openings provided in contact blocks 30a and 30b. The side openings adjoin openings 32a and 32b, respectively, wherein upon threadable advancement of the locking members 36a and 36b, a locking interface with male connector 60 (i.e., as inserted in recess 40) may be reliably provided. See. FIG. 6B.

Further, the recess 40 and side openings 42a, 42b may be defined so as to facilitate sealable interconnection between the contact blocks 30a, 30b and the male connector 60, as well as sealable locking interconnection between the locking members 36a, 36b, contact blocks 30a, 30b, and male connector 60. In the former regard, sealing caps 38a and 38b may be utilized for snap-in engagement with the openings 42A and 42B within the support structure 10. Such sealing caps 38a and 38b may be fabricated from, for example, a resilient material. To enhance a seal between the caps 38A, 38B and their respective openings 42A, 42B, each opening 42A, 42B may include a sealing ring (e.g., an o-ring) about the periphery of its opening. To further ensure the establishment of an appropriate sealed interface between the male and female connectors, annular sealing rings 70 may be disposed along the recess 40. These sealing rings 70 may sealably mate with an outside surface of the male connector 60 when the connector is disposed within the recess 40.

Referring now to FIG. 5, the male connector 60 will be further described. Connector 60 includes a solid tip electrode 62, a cylindrical insulator ring 64 and a cylindrical sleeve electrode 66. The tip electrode 62 and sleeve electrode 66 are each constructed from a conductive material (e.g., machined titanium, gold, etc.) and are partially, concentrically disposed in the connector 60 for electrical interconnection with first and second internal conductors of the cable 106, respectively.

It should also be noted that the contact blocks 30a, 30b, tip electrode 62, sleeve electrode 66 and locking members 36a, 36b may be fabricated from substantially the same metal to reduce or avoid any galvanic potential therebetween. By way of example, such metal may include, without limitation, titanium, gold or platinum. Such materials may also be utilized to house or coat other implantable components usable in conjunction with the present invention.

Reference will now be made to FIG. 6B which illustrates a partial cut away, top view of the male connector 60 as slidably received within electrical contact blocks 30a and 30b of the connector housing 10. As shown in FIG. 6B, connector 60 is positioned within recess 40 of the connector housing 10. The tip electrode 62 is slidably disposed in the opening of electrical contact block 30a and the sleeve electrode 66 is slidably received through the opening of the electrical contact block 30b. The insulating ring 64 is disposed therebetween to prevent electrical short. Further, locking members 36a and 36b have been threadably tightened through side openings of the electrical contact blocks 30a and 30b, respectively, to securably engage the ring electrode 66 and the tip electrode 62, respectively. For sealing purposes, snap-in sealing caps 38a and 38b have been inserted into the opening 42a, 42b of connector housing 10 to sealably engage sealing rings provided at the rims of the openings 42A, 42B, respectively.

The description provided above for purposes of facilitating an understanding of the various features comprising the present invention. Additional embodiments, modifications and extensions will be apparent to those skilled in the art and are intended to be within the scope of the present invention as defined by the claims which follow.

The invention claimed is:

1. An implantable hearing apparatus for stimulating an auditory component, comprising:
   an implant housing;
   a receiver at least partially disposed within the implant housing and adapted to transcutaneously receive signals;
   a processor disposed within the implant housing and adapted to generate an audio drive signal for actuating an implantable auditory stimulator;
   a first signal cable operatively connected to the signal processor and having a first end connected to said implant housing and a second end fixedly attached to one of a female connector and a male connector, and a second signal cable having an end connected to the other of said female connector and said male connector, said female connector being adapted for selective interconnection to the male connector and comprising:
      a connector housing, wherein one of said second end of the first signal cable and said end of said second signal cable is fixedly attached to a first end of said connector housing; and
      a substantially cylindrical receiving port having an open end and a closed end, said open end extending through said first end of said connector housing, wherein when said male connector is disposed in the receiving port the first and second signal cables are juxtaposed and operatively interconnected for signal transmission therebetween.

2. The apparatus of claim 1, further comprising:
   an implantable hearing instrument component for receiving said audio drive signal via said second signal cable.

3. The apparatus of claim 2, wherein said implantable hearing instrument component is an implantable auditory stimulator selected from a group comprising a middle ear transducer, a cochlear electrole and a nerve stimulator.

4. The apparatus of claim 1, further comprising an implantable auditory stimulator for stimulating an auditory component in response to the audio drive signal, wherein said auditory stimulator is selected from a group comprising a middle ear transducer, a cochlear electrole and a nerve stimulator.

5. The apparatus of claim 4, further comprising:
   an implantable microphone for receiving acoustic signals and providing an output signal in response thereto, wherein said processor is operable to process said output signal to generate said audio signal.

6. The apparatus of claim 5, wherein the auditory stimulator is connected to said second signal cable.

7. The apparatus of claim 5, wherein a central axis of said first signal cable entering said connector housing defines a first reference axis a central axis of said substantially cylindrical receiving port defines a second reference axis.

8. The apparatus of claim 7, wherein said first and second reference axes are parallel.

9. The apparatus of claim 7, wherein a plan view said first and second reference axes intersect.

10. The apparatus of claim 9, wherein an included angle between said first and second reference axes is less than 15 degrees.

11. The apparatus of claim 5, wherein said female connector is fixedly attached to said first end of said first signal cable and said second signal cable is fixedly attached to said male connector.

12. The apparatus of claim 1, further comprising:
an implantable auditory stimulator for stimulating an auditory component in response to the audio drive signal, wherein the auditory stimulator is connected to said second signal cable.

13. The apparatus of claim 12, wherein, when said male connector is disposed in said receiving port of said female signal connector, the first and second cables are electrically connected to provide subcutaneous signal transmission of the audio drive signal between the processor and the implantable auditory stimulator.

14. The apparatus of claim 13, wherein a central axis of one of said second end of said first signal cable and said end of said second cable connects to said connector housing to define a first reference axis, and wherein a central axis of said substantially cylindrical receiving port defines a second reference axis.

15. The apparatus of claim 14, wherein said first and second reference axes are parallel.

16. The apparatus of claim 14, wherein in a plan view said first and second reference axes intersect.

17. The apparatus of claim 16, wherein an included angle between said first and second reference axes is less than 15 degrees.

18. The apparatus of claim 1, wherein said receiving port of said female connector includes at least two internal contact members, wherein said first signal cable includes at least first and second conductor wires connected to said first and second contact members, respectively.

19. The apparatus of claim 1, wherein the male connector includes a tip conductor and a sleeve conductor separated by an insulating ring therebetween, and wherein said first contact member includes an opening therethrough and said second contact member includes an opening therethrough for slidably receiving said tip conductor and sleeve conductor, respectively.

20. The apparatus of claim 1, further comprising:
at least a first locking member insertable through said connector housing of said female connector to selectively lock said male connector and said female connector in an interconnected relationship.

21. The apparatus of claim 1, further comprising:
an implantable microphone operatively connected to said processor.

22. An implantable hearing apparatus for stimulating an auditory component, comprising:
an implantable signal processor disposed in an implantable housing and being adapted to generate an audio drive signal and output the audio drive signal to a first signal cable connected to the implantable housing;
an implantable auditory stimulator adapted to stimulate an auditory component in response to said audio drive signal and, received via a second signal cable connected to the implantable auditory stimulator; and
an in-line connector for electrically connecting said first and second signal cables for signal transmission therebetween, said in-line connector being fixedly connected to one of said first and second signal cables and including a female receiving port having an open end substantially adjacent to the fixedly connected cable for receiving a male connector connected to the other of said first and second signal cables, wherein connected portions of the first and second signal cables are juxtaposed when connected by said in-line connector.

23. The apparatus of claim 22, wherein said female receiving port comprises:
a substantially cylindrical recess having said open end and a closed end, wherein said open end extends through a first end of a connector housing.

24. The apparatus of claim 23, wherein said substantially cylindrical recess defines a first reference axis and a central axis of the signal cable fixedly connected to the in-line connector defines a second reference axis, wherein said first and second reference axes are substantially parallel.

25. A method for use in an implantable hearing instrument, comprising:
affixing an implant housing containing a signal processor adapted to generate an audio drive signal at a first subcutaneous location relative to a patient's skull, wherein said implant housing is connected to a first signal cable having one of a male connector and a female connector fixedly connected to a distal end thereof;
affixing an auditory stimulator adapted to stimulate an auditory component in response to said auditory drive signals at a second subcutaneous location relative to said patient's skull, wherein the auditory stimulator is connected to a second signal cable having the other of the male connector and the female connector fixedly connected to a distal end thereof;
moving one of the first signal cable and the second signal cable substantially parallel to the other of the first signal cable and second signal cables to insert said male connector within a receiving port in said female connector to establish a sealed, electrical interconnection between corresponding internal conductors thereof for passive subcutaneous signal transmission of said auditory drive signal between said processor and said auditory stimulator, wherein distal portions of said first and second signal cables are juxtaposed when said male connector is inserted within said female connector; and
selectively advancing at least a first locking member through an opening in a housing of said female connector to engage the male connector and thereby lock said male connector and said female connector in an interconnected relationship.

26. The method of claim 25, wherein said inserting is performed after said first and second components are secured to said first and second locations.

27. The method of claim 25, wherein, after affixing said implant housing and said auditory stimulator, said first and second signal cables are routed out of an incision prior to said inserting, and wherein after said inserting the male connector into the female connector, the connectors are repositioned into the incision.

* * * * *

UNITED STATES PATENT AND TRADEMARK OFFICE
CERTIFICATE OF CORRECTION

| | | |
|---|---|---|
| PATENT NO. | : 7,822,479 B2 | |
| APPLICATION NO. | : 12/016765 | |
| DATED | : October 26, 2010 | |
| INVENTOR(S) | : Stracener | |

It is certified that error appears in the above-identified patent and that said Letters Patent is hereby corrected as shown below:

Column 12, line 38, delete "cables" and insert therefor --cable--.

Signed and Sealed this
Fourth Day of January, 2011

David J. Kappos
*Director of the United States Patent and Trademark Office*